US00PP10825P

United States Patent [19]

Zerr

[11] Patent Number: Plant 10,825

[45] Date of Patent: Mar. 16, 1999

[54] POINSETTIA PLANT NAMED 'FISSON WHITE'

[75] Inventor: Katharina Zerr, Simmern, Germany

[73] Assignee: Florfis AG, Binnengen, Switzerland

[21] Appl. No.: 854,675

[22] Filed: May 12, 1997

[51] Int. Cl.[6] ..... A01H 5/00

[52] U.S. Cl. ..... Plt./86.2

[58] Field of Search ..... Plt./86.2, 86.1

[56] References Cited

U.S. PATENT DOCUMENTS

P.P. 8,319 7/1993 Dahlquist ..... Plt./86.2
P.P. 8,772 6/1994 Jacobson ..... Plt./86.2

OTHER PUBLICATIONS

GTITM UPOVROM Citation for 'Fisson White' as per CAPBR 96–908, Jul. 12, 1996.
GTITM UPOVROM Citation for 'Fisson White' as per JP PBR 9137, Sep. 17, 1996.

*Primary Examiner*—Howard J. Locker
*Assistant Examiner*—Kent L. Bell
*Attorney, Agent, or Firm*—Foley & Lardner

[57] ABSTRACT

A new and distinct cultivar of poinsettia plant named 'Fisson White', characterized by its uniform cream-white to white distinctly lobed bracts, distinctly lobed dark green foliage, compact, bushy and well branched growth habit, medium early flower response, and good post-production keeping quality.

1 Drawing Sheet

The present invention relates to a new and distinct cultivar of poinsettia plant, known by the cultivar name 'Fisson White', and botanically known as *Euphorbia pulcherrima.*

'Fisson White' is a product of a mutation induction program carried out by the inventor, Katharina Zerr, in Hillscheid, Germany, in 1994. The primary objective of the induction program was to expand the bract color ranges of 'Fisson', a cultivar disclosed in U.S. Plant Pat. No. 9,365 and characterized by its dark red bract color, dark green foliage and comparatively compact habit.

The irradiation program comprised exposing rooted cuttings taken from plants of the parent cultivar to an X-ray source of 30 Gy dosage in Ahrensburg, Germany, under the supervision of the inventor. The irradiated plants were grown out in a greenhouse in Hillscheid, Germany, and were asexually propagated by taking cuttings. The plants resulting from these cuttings were screened for mutations as small flowering single stem plants in autumn and winter 1994, and those discovered were identified by numbers.

'Fisson White' was derived from a partially mutated plant (designated No. 183) which had about half of its involucre turned white, and was discovered by the inventor in December 1994. The mutated area of the plant was left to develop vegetative shoots, which were used as cuttings and grown out. Through subsequent asexual propagation and selection, by or under the supervision of the inventor, a uniform clone with white bracts was developed.

The clone was examined and compared to other clones in a trial cultivation in summer 1995 and, on a larger scale, in autumn 1995. Horticultural examination has confirmed that the combination of characteristics disclosed for 'Fisson White' are firmly fixed and are retained through successive generations of asexual reproduction.

The following traits have been repeatedly observed and are determined to be basic characteristics of 'Fisson White' which in combination distinguish this poinsettia as a new and distinct cultivar:

1. Uniform cream-white to white bract color
2. Flat involucre with distinctly lobed, medium sized bracts;
3. Dark green foliage, with distinctly lobed leaves;
4. Compact, bushy and very well branched habit, making the plant well suited for production of branched pot plants;
5. Medium early flowering response; and 6. Good keeping quality and resistance to leaf and bract drop.

'Fisson White' has not been observed under all possible environmental conditions. The phenotype may vary significantly with variations in environment such as temperature, light intensity, and daylength without, however, any variance in genotype. The following observations, measurements and comparisons describe plants grown in Hillscheid, Germany, under greenhouse conditions which approximate those generally used in commercial practice.

Of the many commercial cultivars known to the inventor, the most similar in comparison to 'Fisson White' are the parent cultivar 'Fisson', and the commercial varieties 'Freedom White' (U.S. Plant Pat. No. 8,772) and 'Lilo White' (U.S. Plant Pat. No. 8,319). The new variety is also similar to 'Fisson Marble', which is described in co-pending U.S. Plant patent application Ser. No. 08/854,674.

In contrast to the bright red colored bracts of the parent 'Fisson', 'Fisson White' has cream-white to white bracts and light green petioles without anthocyanin. Other morphological characteristics are very similar.

In comparison to 'Lilo White', 'Fisson White' has differently shaped bracts, its leaves have wedge-shaped bases and strong lobes, and the pinched plants of 'Fisson White' are by far better branched. In addition, the flowering response of 'Fisson White' is not quite as early, and the cyathia retention is better.

In comparison to 'Freedom White' 'Fisson White' has smaller bracts with a more smooth surface and stronger lobed margin. In addition, in 'Fisson White' the flower response is somewhat later, development and retention of the cyathia is better, and 'Fisson White' usually grows more compact.

In comparison to 'Fisson Marble' 'Fisson White' has white bracts, light green leaf petioles, and white or slightly greenish brack petioles. 'Fisson Marble' has white and pink brack, pink-infused light green leaf petioles, and pink-lined, very light green bract petioles. 'Fisson Marble' has also been repeatedly observed to be slightly taller, about 23 cm, than 'Fisson White', about 20 cm.

The accompanying color photographic drawing comprises a side elevational view showing typical inflorescence and foliage of 'Fisson White', with colors being as true as possible with illustrations of this type. The photograph shows a typical mature potted plant.

In the following description, color references are made to The Royal Horticultural Society Colour Chart. The bract color values were determined indoors in a north light at temperatures of 17° C. at which the white bract color is somewhat less pure.

The description is based on plants which were planted as rooted cuttings in 12 cm pots on August 24 and pinched 14 days later leaving 8 nodes, and grown at 17°–20° C. minimum day and night temperatures. The plants initiated flowers under natural short day conditions in autumn 1995. Observations and measurements were mainly taken at the beginning of flowering.

Classification:

*Botanical.*—*Euphorbia pulcherrima.*

*Commercial.*—Poinsettia, cv. 'Fisson White'.

Parentage: Induced mutation of 'Fisson White'.

Plant description:

*Form.*—Shrub, self-branching.

*Growth habit.*—Compact, and very well branched; pinched plants are bushy and round shaped; weak to medium growth; Height (above the soil line): 20.0 cm. Diameter/width: 40.0 cm. Average no. of branches: 7.5.

*Stem color.*—Solid green with no anthocyanin.

*Rooting.*—Medium, 20 days.

*Blooming Habit.*—The commencement of flowering under natural short day conditions in autumn: Botanically (cyathia open): in early December. Commercially (bracts colored, marketable): in late November. Flowering response time: about 9 weeks.

*Foliage.*—Flowering season and keeping quality: Under winter conditions in Central Europe, commercial quality will be maintained for about 4–6 weeks from date when plant is ready for sale in late November; however, under controlled conditions with sufficient light intensity, the flowering period may be expanded by several weeks; leaf and bract retention is generally better under poor light conditions than that of most varieties with medium green foliage. Shape: Roughly triangular, with acute base, strong pointed lobes, rounded sinus between the lobes, and acuminated tip; smaller leaves without lobes are broad elliptical. Size: Leaf blade: Length: 13.5 cm. Width: 9.0 cm (lobed leaf). Petiole: 5.0 cm. Color: Generally dark green. Upper surface: about 139 A. Under surface: about 137 B. Leaf petiole: Light green, about 147 D, Texture: Upper surface smooth and flat. Edge of margin: Entire.

*Leaf surface and venation.*—Upper surface: Smooth and flat, only weakly veined with light green, about R.H.S. 146 D. Under surface: Flat and smooth, except for the slightly protruding midrib and finer side veins, which protrude at an acute, almost right angle from the midrib; the side veins are evenly spread throughout the leaf blade and run parallel to each other; vein color is R.H.S. 145 C.

Flowering description:

*Cyathia.*—In a narrow cluster, few (about 10–14); retention, is average when compared to similar cultivars or this variety; color, light to medium green, top yellow to whitish.

*Bracts.*—Larger bracts are roughly triangular in shape, with acute base, strong pointed lobes, rounded sinus between the lobes, and acuminated tip.

*Bract venation and color.*—The bracts are smooth and flat with veins hardly visible during dehiscence. As bract leaves mature, veins create a more rugose pattern similar to the foliage leaves. Vein color corresponds closely to bract color, upper surface veins are 10 D and lower surface veins are 4 D. Mature, fully colored bracts tend to keep their color, fading very little. Bracts that are still growing may become green within about 3 weeks when the plants are exposed to long-day conditions, depending primarily on light intensity.

*Surface.*—Flat or slightly folded, occasionally somewhat rugose.

*Size.*—Largest bract with petiole: 13.0 cm; bract length is about 11.5 cm; petiole length is about 1.5 cm; and bract width is about 10.3 cm.

*Color.*—Cream white to white. Upper surface: 2 D. Lower surface: 4 C .

*Petiole.*—White or very light green, about 10 D or 145 C.

*Aspect.*—Horizontal, forming a flat involucre with tips slightly overhanging and center not always closed at the beginning of flowering.

Reproductive organs:

*Nectar cups.*—Small to medium sized, yellow.

*Stamens.*—Filaments are whitish.

*Pollen.*—Yellow, abundant.

*Pistils.*—Style and stigma cream white, 6 lobed stigma.

*Ovaries.*—Light to medium green, triangular, 3-celled, 3 ovules.

I claim:

1. A new and distinct cultivar of poinsettia plant named 'Fisson White', as illustrated and described.

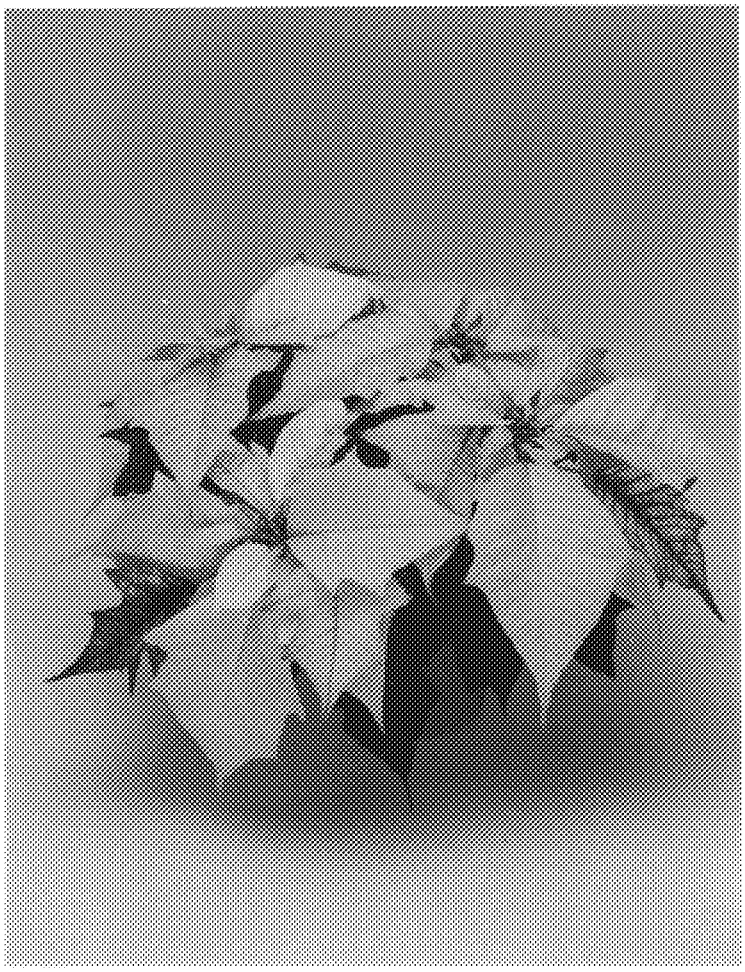

* * * * *